United States Patent [19]

Kohn et al.

[11] 3,978,173

[45] Aug. 31, 1976

[54] PREPARATION OF O,S-DIMETHYL PHOSPHOROAMIDOTHIOATES

[75] Inventors: Gustave K. Kohn, Berkeley; Irene C. Huang, Castro Valley; William G. Toland, San Rafael, all of Calif.

[73] Assignee: Chevron Research Company, San Francisco, Calif.

[22] Filed: Nov. 29, 1974

[21] Appl. No.: 528,300

[52] U.S. Cl. .............................. 260/984; 260/972
[51] Int. Cl.² .................................... C07F 9/24
[58] Field of Search ........... 260/984, 972, 959, 960, 260/985

[56] References Cited
UNITED STATES PATENTS 3,489,825   1/1970   Aichenegg ................... 260/984 X

FOREIGN PATENTS OR APPLICATIONS 395,372   12/1973   U.S.S.R.

OTHER PUBLICATIONS

Houben–Weyl, Methoden der Organischen Chemie, vol. 11/2 (1964), pp. 621, 622 and 771.

Primary Examiner—Richard L. Raymond
Attorney, Agent, or Firm—George F. Magdeburger; Dix A. Newell; Raymond Owyang

[57]  ABSTRACT

O,S-dimethyl phosphoroamidothioates are prepared by reacting in the liquid phase methyl phosphorodichloridite with methyl sulfenyl chloride in the presence of a lower alkanoic acid to produce O,S-dimethyl phosphorochloridothioate and subsequently reacting in the liquid phase the O,S-dimethyl phosphorochloridothioate with ammonia or an amine.

11 Claims, No Drawings

PREPARATION OF O.S.-DIMETHYL PHOSPHOROAMIDOTHIOATES

FIELD OF THE INVENTION

This invention relates to a new process for the preparation of the commercial insecticide O,S-dimethyl phosphoroamidothioate, which is described in U.S. Pat. Nos. 3,309,266 and 3,676,555.

DESCRIPTION OF THE PRIOR ART

J. R. Sanborn and T. R. Fukuto, *J. Agr. Food Chem.*, 20, 926 (1972), describe the preparation of O-ethyl S-phenyl phosphoroamidothioates by reacting an O-ethyl S-phenyl phosphorochloridothioate with ammonia or an amine.

DESCRIPTION OF THE INVENTION

Insecticidal O,S-dimethyl phosphoroamidothioates of the formula (I)

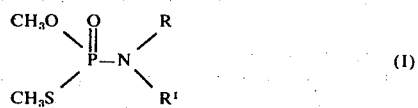

wherein R and R¹ individually are hydrogen or alkyl of 1 to 6 carbon atoms, preferably 1 to 3 carbon atoms, are prepared by a high-yield process beginning with methyl phosphorodichloridite.

The process may be depicted by the following reactions:

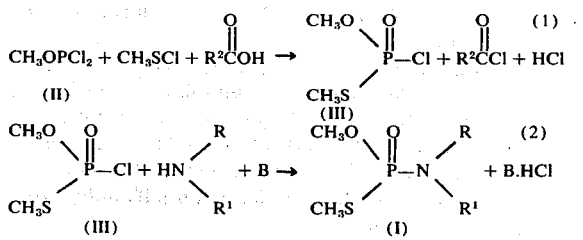

wherein R and R¹ have the same significance as defined in formula (I), R² is lower alkyl, and B is an acid acceptor.

Reaction (1) is conducted by reacting in the liquid phase substantially equimolar amounts of the methyl phosphorodichloridite (II), methyl sulfenyl chloride and a lower alkanoic acid e.g., molar ratio of phosphorodichloridite to methyl sulfenyl chloride generally varies from about 1.2:1 to 1:1.2 and molar ratio of phosphorodichloridite to alkanoic acid generally varies from about 1.2:1 to 1:1.2.

Examples of suitable alkanoic acids include acetic, propionic and isobutyric acid.

Reaction (1) can be carried out in inert diluents such as aromatic hydrocarbons, e.g., benzene, toluene and xylene, or chlorinated alkanes and aromatic compounds, e.g., methylene chloride, chloroform, carbon tetrachloride, chlorobenzene, etc. Excess alkanoic acid can also be used as the reaction diluent. However, the preferred reaction diluents are chlorinated alkanes.

To obtain good yields of O,S-dimethyl phosphorochloridothioate Reaction (1) should be conducted at reduced temperatures, e.g., from about −75°C to 25°C, preferably from about −75°C to 10°C, and under essentially anhydrous reaction conditions. The reaction is generally carried out at atmospheric pressure, although super- or subatmospheric pressure may be utilized, if desired. The reaction time varies from several minutes to several hours, depending upon the reaction temperature.

After completion of Reaction (1), the volatile by-products, i.e., the hydrogen chloride and alkanoyl chloride, should be essentially completely, e.g., greater than 90%, separated or removed from the O,S-dimethyl phosphorochloridothioate product prior to using the O,S-dimethyl phosphorochloridothioate in Reaction (2). Preferably, the by-products are removed by evaporation under reduced pressure and at a temperature about 25°C or below. The by-products can also be removed by passing an inert gas such as nitrogen into the product mixture of Reaction (1). However, by any method of by-products separation or removal, it is essential that the separation or removal be accomplished without subjecting the O,S-dimethyl phosphorochloridothioate to elevated temperatures. O,S-phosphorochloridothioate appears to undergo an autocatalytic decomposition which is accelerated by elevated temperatures or moisture. For example, substantially lower yields of O,S-dimethyl phosphorochloridothioate are obtained when the O,S-dimethyl phosphorochloridothioate is distilled overhead at elevated temperatures. The residence time at the higher temperature required for overhead distillation apparently results in the decomposition of the O,S-dimethyl phosphorochloridothioate compound.

Reaction (2) is conducted in the liquid phase by reacting the O,S-dimethyl phosphorochloridothioate and a nitrogen base selected from ammonia, a lower alkylamine and a lower dialkylamine in the presence of an acid acceptor. To obtain high yields of the O,S-dimethyl phosphoroamidothioate product (I) it is essential that the O,S-dimethyl phosphoroamidothioate reactant be contacted with the nitrogen base at ambient temperatures or below, e.g., below about 25°C, more preferably below 10°C and under essentially anhydrous reaction conditions to prevent decomposition of the O,S-dimethyl phosphoroamidothioate reactant.

The O,S-dimethyl phosphorochloridothioate (VII) and nitrogen base (X) are employed in substantially equimolar amounts, e.g., the molar ratio of phosphorochloridothioate to nitrogen base generally varies from about 1:1 to 1:1.5, although a molar ratio of phosphorochloridothioate to nitrogen base of about 1:1 to 1:1.2 is preferred. The molar ratios of phosphorochloridothioate to acid acceptor are also substantially equimolar, e.g., the molar ratio of phosphorochloridothioate to acid acceptor varies from about 1.1:1 to 1:1.5, although a molar ratio of phosphorochloridothioate to acid acceptor from about 1.1:1 to 1:1.2 is preferred.

The acid acceptor is an inorganic base, e.g., alkali metal bicarbonate or carbonate, or an organic nitrogen base having no N-H group, such as a pyridine compound or a trialkylamine. Suitable pyridine compounds are pyridine and pyridine compounds of 6 to 10 carbon atoms and of 1 to 2 alkyl groups such as 2-methylpyridine, 2-ethylpyridine, 3-methylpyridine, 3,5-dimethylpyridine, and 2-butylpyridine. Suitable trialkylamines are those wherein the alkyl group contains individually 1 to 4 carbon atoms, such as trimethylamine, triethylamine, tripropylamine and tributylamine. In a preferred modification of the reaction, the nitrogen base reactant, i.e., ammonia, lower alkylamine or lower dialkylamine, is employed as the acid acceptor. In this modification, at least about two mols of the nitrogen base are employed per mol of O,S-dimethyl phosphorochloridothioate, e.g., the molar ratio of phosphorochloridothioate to nitrogen base generally varies from about 1:2 to 1:3.

Reaction (2) is preferably carried out in an inert organic solvent to facilitate the cooling of the reaction mixture to the required reduced temperatures specified above. Suitable organic solvents include aromatic hydrocarbons such as benzene and toluene, and chlorinated alkanes such as methylene chloride, chloroform and carbon tetrachloride. Reaction pressure is not critical, so long as the reaction mixture is maintained substantially in a non-gaseous phase. Typical pressures vary from 1 to 10 atmospheres. Completion of the reaction is indicated by the cessation of ammonium chloride or amine hydrochloride precipitation. In general, the reaction is complete within several minutes.

Following the reaction, the O,S-dimethyl phosphoroamidothioate product (I) can be isolated by conventional methods such as filtration, crystallization, extraction, chromatography, etc.

EXAMPLES

EXAMPLE 1 — Preparation of O,S-dimethyl phosphoroamidothioate

Methanol (32 g, 1 mol) was added slowly to 137.3 g (1 mol) phosphorus trichloride with vigorous stirring at a temperature of about −40°C over a 2½ hour period. After the addition was completed, the reaction mixture was warmed to room temperature and then distilled to give 61.6 g of methyl phosphorodichloridite, b.p. 88°–92°C. The nuclear magnetic resonance (NMR) spectrum of the product showed only a 3-proton doublet ($CH_3O-$) centered at 3.75 ppm (relative to tetramethylsilane).

A solution of 20 g (0.24 mol) methyl sulfenyl chloride (prepared from dimethyl disulfide and sulfuryl chloride) in 30 ml chloroform was added dropwise to a cooled (−60°C) solution of 14.5 g (0.24 mol) acetic acid and 32.2 g (0.24 mol) methyl phosphorodichloridite (prepared above) in 20 ml chloroform. The reaction mixture was protected from atmospheric moisture with a calcium sulfate drying tube. After the addition was completed, the reaction temperature was allowed to warm to room temperature and nitrogen was bubbled into the reaction mixture. The reaction was then evaporated under reduced pressure at about 25°C to give 39.5 g (38.9 g theoretical yield) of crude O,S-dimethyl phosphorochloridothioate. The NMR spectrum of the product showed a 3-proton doublet centered at 2.3 ppm and a 3-proton doublet centered at 3.8 ppm (relative to tetramethylsilane).

A solution of about 1 g (0.06 mol) ammonia in 20 ml chloroform was added dropwise to an ice bath-cooled solution of 4 g (0.02 mol) O,S-dimethyl phosphorochloridothioate (freshly prepared as described above) in about 30 ml of chloroform. A white precipitate of ammonium chloride was formed. After the addition was completed the reaction mixture was stirred for 20 minutes and then filtered. The filtrate was evaporated under reduced pressure to give 2.7 g O,S-dimethyl phosphoroamidothioate, which solidified on standing. After crystallization from ether, the O,S-dimethyl phosphoroamidothioate product melted at 39°–40°C. The yield based on methyl phosphorodichloridite was 71%.

O,S-dimethyl phosphoroamidothioate is an insecticide commercially sold as MONITOR Insecticide.

EXAMPLE 2 — Preparation of O,S-dimethyl phosphorochloridothioate

O,S-dimethyl phosphorochloridothioate was prepared in two experiments from methyl phosphorodichloridite, methyl sulfenyl chloride and acetic acid in chloroform reaction diluent by a procedure similar to that of Example 1 except that the O,S-dimethyl phosphorochloridothioate product was purified and isolated by overhead vacuum distillation through a short column at a bath temperature of about 90°C. O,S-dimethyl phosphorochloridothioate yields of 5 to 20% based on methyl phosphorodichloridite were obtained.

The low yield procedure of this example is similar to that disclosed by U.S.S.R. Patent 393,372 [API Patent Alert Abstract No. 74-91890] for the preparation of O,S-dialkyl and O,S-dihaloalkyl phosphorochloridothioates.

What is claimed is:

1. A process for preparing O,S-dimethyl phosphoroamidothioate compounds which comprises:
   a. reacting substantially equimolar amounts of (1) methyl phosphorodichloridite, (2) methyl sulfenyl chloride and a lower alkanoic acid, in the liquid phase under essentially anhydrous reaction conditions at a temperature of about −75° to 25°C;
   b. removing essentially completely the resulting alkanoyl chloride and hydrogen chloride at a temperature below about 25°C to prevent decomposition of the resulting O,S-dimethyl phosphorochloridothioate product; and
   c. reacting the O,S-dimethyl phosphorochloridothioate with a substantially equimolar amount of a nitrogen base selected from ammonia, a lower alkylamine or lower dialkylamine, in the liquid phase in the presence of an acid acceptor at a temperature below about 25°C under essentially anhydrous reaction conditions.

2. The process of claim 1 wherein the alkanoyl chloride and hydrogen chloride are removed by evaporation under reduced pressure.

3. The process of claim 1 wherein the nitrogen base is used as the acid acceptor and the molar ratio of O,S-dimethyl phosphorochloridothioate to nitrogen base is from about 1:2 to 1:3.

4. The process of claim 1 wherein the nitrogen base and acid acceptor are ammonia.

5. The process of claim 1 wherein an inert diluent is employed in the reaction of the methyl phosphorodichloridite.

6. The process of claim 1 wherein an inert diluent is employed in the reaction of the O,S-dimethyl phosphorochloridothioate.

7. A process for preparing O,S-dimethyl phosphoroamidothioate which comprises:
   a. reacting substantially equimolar amounts of methyl phosphorodichloridite, methyl sulfenyl chloride and acetic acid in the liquid phase under essentially anhydrous reaction conditions at a temperature of −75°C to 25°C;
   b. evaporating the resulting reaction mixture under reduced pressure and at a temperature about 25°C or below to give a residue consisting essentially of O,S-dimethyl phosphorochloridothioate; and c. reacting the residue with at least about 2 mols, per mol of O,S-dimethyl phosphorochloridothioate, of ammonia in the liquid phase at a temperature below about 25°C under essentially anhydrous reaction conditions.

8. The process of claim 7 wherein the reaction of the methyl phosphorodichloridite is conducted in an inert diluent under essentially anhydrous reaction conditions.

9. The process of claim 8 wherein the diluent is a chlorinated alkane.

10. The process of claim 7 wherein the reaction of the O,S-dimethyl phosphorochloridothioate is conducted in an inert diluent.

11. The process of claim 10 wherein the diluent is a chlorinated alkane.

* * * * *